(12) United States Patent
Beder (10) Patent No.: US 12,376,990 B2
(45) Date of Patent: Aug. 5, 2025

(54) OPTICAL SYSTEM FOR EYE SURGERY AND METHOD FOR AVOIDING AN EXCESSIVE LIGHT INTENSITY AT A DIGITAL IMAGE SENSOR OF A SURGICAL MICROSCOPE

(71) Applicant: Carl Zeiss Meditec AG, Jena (DE)

(72) Inventor: Christian Beder, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 694 days.

(21) Appl. No.: 17/700,078

(22) Filed: Mar. 21, 2022

(65) Prior Publication Data

US 2022/0304849 A1 Sep. 29, 2022

(30) Foreign Application Priority Data

Mar. 24, 2021 (DE) ...................... 10 2021 107 297.2

(51) Int. Cl.
*A61B 3/13* (2006.01)
*A61B 90/20* (2016.01)
(Continued)

(52) U.S. Cl.
CPC ................ *A61F 9/007* (2013.01); *A61B 3/13* (2013.01); *A61B 90/20* (2016.02); *A61B 90/30* (2016.02);
(Continued)

(58) Field of Classification Search
None
See application file for complete search history.

(56) References Cited

U.S. PATENT DOCUMENTS 9,829,692 B2 11/2017 Reimer et al.
10,292,783 B2 5/2019 Bacher et al.
(Continued)

FOREIGN PATENT DOCUMENTS

DE 10 2009 017 710 B4 10/2010
WO WO-2009/002574 A2 12/2008
(Continued)

OTHER PUBLICATIONS

Moura-Coelho et al., "Three-dimensional Display Systems in Ophthalmic Surgery—A Review," European Ophthalmic Review, vol. 13, Jul. 2019, No. 1, pp. 31-36.
(Continued)

*Primary Examiner* — Eileen M Adams
(74) *Attorney, Agent, or Firm* — NIXON PEABODY LLP; Jeffrey L. Costellia (57) ABSTRACT

An optical system for eye surgery, comprising at least a surgical microscope, an illumination unit for emitting illumination light, and a control unit.
The surgical microscope is configured to output an observation mode signal indicating the employed observation mode and a mode-of-operation signal indicating the employed mode of operation, and the control unit is configured to receive the observation mode signal and the mode-of-operation signal from the surgical microscope and to output a change signal which prompts a change in the amount of light received by the at least one digital image sensor. The change signal is output only if the received observation mode signal and the received mode-of-operation signal indicate a predetermined combination of observation mode and mode of operation.

15 Claims, 2 Drawing Sheets

(51) Int. Cl.
      *A61B 90/30*       (2016.01)
      *A61F 9/007*       (2006.01)
      *G02B 21/00*       (2006.01)
      *H04N 23/667*       (2023.01)
      *H04N 23/50*       (2023.01)
      *H04N 23/56*       (2023.01)

(52) U.S. Cl.
      CPC ........ *A61F 9/0079* (2013.01); *G02B 21/0012* (2013.01); *H04N 23/667* (2023.01); *H04N 23/555* (2023.01); *H04N 23/56* (2023.01)

(56) References Cited

U.S. PATENT DOCUMENTS

2014/0340500 A1* 11/2014 Hoegele ................. G02B 21/22
                                                                                359/377
2019/0357980 A1* 11/2019 Andrews ................. A61B 3/102
2020/0302610 A1*  9/2020 Yamada ............... G02B 21/365
2022/0257416 A1*  8/2022 Foulkes ............. A61F 9/00736
2023/0404400 A1* 12/2023 Yamada .................... A61B 3/13

FOREIGN PATENT DOCUMENTS

WO    WO-2009/009165 A2    1/2009
WO    WO-2020/170866 A1    8/2020

OTHER PUBLICATIONS

German Search Report for Application No. 10 2021 107 297.2 mailed Nov. 30, 2021, 16 pages.

* cited by examiner

OPTICAL SYSTEM FOR EYE SURGERY AND METHOD FOR AVOIDING AN EXCESSIVE LIGHT INTENSITY AT A DIGITAL IMAGE SENSOR OF A SURGICAL MICROSCOPE

CROSS-REFERENCE TO RELATED APPLICATIONS

The present application claims the benefit of and priority to German Patent Application No. 10 2021 107 297.2, filed Mar. 24, 2021, the contents of which are hereby incorporated by reference herein in their entirety.

The present invention relates to an optical system for eye surgery comprising at least a surgical microscope, an illumination unit for illuminating the eye, and a control unit, and to a method for reducing the light intensity at a digital image sensor of a surgical microscope in such a system.

In the case of posterior segment surgery on the eye, illumination is usually implemented by means of an endoilluminator which comprises a light guide introduced into the eye, since external illumination through the pupil would render the image unusable for the surgeon on account of too many bothersome reflections. By way of example, illumination by means of an endoilluminator is used when removing the vitreous humor of the eye (vitrectomy). In this case, the brightness of the illumination supplied by means of the endoilluminator needs to be so bright that a sufficiently bright image arises for the surgeon but, at the same time, it must not be so bright that there is damage to the retina of the eye.

When the eye is observed through the eyepiece of a surgical microscope, the minimum brightness of the illumination required is determined predominantly by the sensitivity of the eyes of the surgeon. If the brightness is too low, the surgeon simply is unable to recognize enough. Relatively recent surgical microscope generations however facilitate an electronically imparted observation in addition to the purely visual observation through the eyepieces. To this end, novel surgical microscopes comprise image sensors which record a 3-D image and one or more displays on which the recorded 3-D image can be represented. In that case, the surgeon has the choice of whether they wish to observe the eye purely visually through the tube and the eyepieces or whether they wish to observe the 3-D image on the monitor by means of 3-D glasses. In the latter option, however, the sensitivity of the employed image sensors is so high that the monitor image already has a brightness sufficient for the surgeon in the case of a much lower illumination intensity by way of the endoilluminator. In this case, the illumination intensity can be reduced from approximately 80 percent of the maximum intensity in the case of a purely visual observation to approximately 10 percent of the maximum intensity, sparing the retina of the eye to be treated.

As a rule, the illumination intensity of an endoilluminator can be adjusted in steps of 5 percent, and so 20 illumination levels are present between the maximum intensity and the minimum intensity. If the illumination intensity is now for instance set to a value from an intensity range between 5 percent to 15 percent of the maximum intensity, only very few illumination levels of these 20 illumination levels remain for this intensity range, for example 5 percent, 10 percent and 15 percent, however, and so the illumination intensity for a 3-D image represented on the monitor virtually cannot be adjusted or can only be adjusted very coarsely. Moreover, if particularly sensitive image sensors are used, the minimum intensity to be set on the endoilluminator may already be too high, the consequence of which being that the 3-D image represented on the monitor is too bright.

The use of less intensive light sources is out of the question since the surgical microscope should continue to offer the option of a purely visual observation through the tube and the eyepieces. In practice, it was found that there is a switching back and forth between visual observation and digitally assisted observation, both during an operation and between successive operations or when changing from one surgeon to the next. Moreover, the surgical microscopes are typically used not only for posterior segment surgery on the eye but also for other treatment purposes, for which a higher illumination intensity is required.

U.S. Pat. No. 10,292,783 B2, WO 2009/002574 A2 and WO 2009/009165 A2 have disclosed endoilluminators in which an illumination intensity suitable for the respective treatment can be set by means of attenuators.

It is an object of the present invention to provide an optical system for eye surgery and a method, by means of which an excess image brightness on a display or displays can be avoided in the case of digital image recording and observation of the image on the one or more displays.

The aforementioned object is achieved by an optical system for eye surgery as claimed in claim 1 and by a method as claimed in claim 10 for reducing the amount of light received by a digital image sensor. The dependent claims contain advantageous configurations of the invention.

According to a first aspect of the invention, an optical system for eye surgery, comprising at least a surgical microscope, an illumination unit for emitting illumination light, and a control unit is made available. In this case, the surgical microscope comprises:

at least one digital image sensor,
  at least one eyepiece,
  a digital observation mode in which a digital image of the observation region is created using the at least one digital image sensor, said image being observed by way of at least one display,
  a non-digital observation mode in which the observation region is observed through the at least one eye piece without digital means being interposed, and
  at least two modes of operation.

The surgical microscope is configured to output an observation mode signal indicating the observation mode and a mode-of-operation signal indicating the mode of operation.

The control unit is configured to receive the observation mode signal indicating the observation mode and the mode-of-operation signal indicating the mode of operation from the surgical microscope. Moreover, it is configured to output a change signal which prompts the change in the amount of illumination light received by the at least one digital image sensor. Here, the control unit is configured to output the change signal only if the received observation mode signal and the received mode-of-operation signal indicate a predetermined combination of observation mode and mode of operation.

Setting the illumination intensity of an endoilluminator to an illumination intensity suitable for the respective treatment, as known from the prior art set forth at the outset, does not lead to a satisfactory result in all cases. Especially if the observation of the observation object can be selectively implemented in purely visual fashion or using digital image sensors, it is not sufficient to adjust the illumination intensity of an endoilluminator to an illumination intensity suitable for the respective treatment. This is because the same treatment requires very different illumination intensities depending on the observation mode (purely visual or digital), as was presented at the outset. The optical system according to the invention therefore provides means which can improve the adjustment options. By way of example, there may be a targeted adjustment of the illumination intensity as a result of the illumination intensity being set not only on the basis of the adjusted mode of operation that signals a certain treatment but being set on the basis of one or more defined combinations of mode of operation and observation mode. Moreover, the change signal in this case need not necessarily act on the illumination intensity but may also act on the exposure duration of the at least one digital image sensor in order to generate a suitable image brightness on the utilized display.

In a special embodiment variant of the invention, one of the modes of operation is a mode of operation for posterior segment surgery. In this embodiment variant, the change signal is suitable for prompting a reduction in the amount of light received by the at least one digital image sensor, the output of the change signal requiring that the mode-of-operation signal indicates the mode of operation for posterior segment surgery and the observation mode signal indicates the digital observation mode. In the case of posterior segment surgery using digital image sensors and one or more displays for the surgeon, this embodiment variant of the optical system according to the invention facilitates the adjustment of a suitable amount of light received by a digital image sensor. An excessively bright image on the at least one display can be reliably avoided thereby. The automated recognition of the combination of posterior segment surgery with digital observation of the observation region in this case facilitates quick and uncomplicated setting of the suitable amount of light received by the image sensor, and moreover assists in the avoidance of incorrect settings. In this embodiment variant, the indication of the mode of operation for posterior segment surgery by the mode-of-operation signal can be triggered by for example pivoting an ophthalmic loupe into the observation beam path. To facilitate this, the surgical microscope can be configured to recognize whether an ophthalmic loupe has been pivoted into the observation beam path and to output the mode-of-operation signal indicating the mode of operation for posterior segment surgery upon recognition of an ophthalmic loupe pivoted into the observation beam path. Since, as a rule, an ophthalmic loupe is pivoted-in anyway in the case of posterior segment surgery, this pivoting-in lends itself to being used as the trigger for the output of a mode-of-operation signal indicating posterior segment surgery. In this case, pivoting-in of the ophthalmic loupe is a reliable indicator for posterior segment surgery being implemented.

In particular, the illumination unit of the optical system can be an endoilluminator with a light guide that is able to be introduced into the eye for the purposes of illuminating the posterior segment of the eye. Such an endoilluminator facilitates the targeted illumination of the posterior segment without bothersome reflections and with the minimally required illumination intensity. In this case, an optical fiber or a light-guiding rod can find use as a light guide.

To realize the change in the amount of illumination light received by the digital image sensor following the change signal, an image sensor controller may be assigned to the at least one digital image sensor to which image sensor controller the control unit for outputting the change signal is connected. The change signal is output from the control unit to the image sensor controller. The image sensor controller is configured to change for example the exposure duration of the at least one digital image sensor upon reception of the change signal. In the case of the "posterior segment surgery" mode of operation, this change consists of for example a reduction in the exposure duration if the mode-of-operation signal indicates the mode of operation for posterior segment surgery and the observation mode signal indicates the digital observation mode. In this embodiment of the optical system, the invention can be realized without having to make changes to the illumination unit. As a rule, image sensor controllers are present in any case, and so available optical systems can be retrofitted, optionally by way of a software update, into optical systems according to the invention.

In an alternative embodiment of the optical system according to the invention, the illumination unit has an apparatus for controllably changing the illumination intensity. In this case, the control unit is configured to output the change signal to for example the apparatus for controllably changing the illumination intensity, the apparatus for controllably changing the illumination intensity being configured to change the illumination intensity upon reception of the change signal. To this end, a first alternative of the apparatus for controllably changing the illumination intensity can comprise at least one attenuator which is able to controllably be introduced into the illumination beam path of the illumination unit or controllably be removed therefrom, the apparatus for controllably changing the illumination intensity being configured to introduce the attenuator into the illumination beam path or remove it therefrom upon reception of the change signal. By way of example, the attenuator can be a neutral density filter or a sieve aperture. By way of example, for the purposes of introducing the attenuator into the illumination beam path there may be a filter wheel with a filter wheel opening having the attenuator and with a clear filter wheel opening. Furthermore, there is the option of arranging the attenuator on a pivoting apparatus which allows the attenuator to be controllably pivoted into the illumination beam path or to be pivoted out of the illumination beam path. In the case of an attenuator which is able to be introduced into the illumination beam path, it is moreover advantageous if the apparatus for controllably reducing the illumination intensity facilitates a replacement of the attenuator in order to be able to adapt the apparatus to even more sensitive digital image sensors, for example by way of a stronger attenuator. Instead of an attenuator which is able to be introduced into the illumination beam path of the illumination unit, or in addition thereto, the apparatus for controllably changing the illumination intensity may however also comprise a stop with a controllably variable aperture arranged in the illumination beam path of the illumination unit, said stop being configured to alter the aperture upon reception of the change signal. By way of example, an iris diaphragm can be used as a stop with a variable aperture.

Changing the illumination intensity is advantageous over a change in the exposure duration of the digital image sensor in that it is not only possible to avoid an excessively bright image on the display or displays when the illumination intensity is reduced, but that the retina of the eye is spared by the reduced illumination intensity at the same time. However, in comparison with changing the amount of light received by the digital image sensor by changing the exposure duration, the change in the illumination intensity however requires a structural adaptation of the illumination unit.

According to a second aspect of the invention, a method is provided for changing the amount of light received by a digital image sensor in an optical system for eye surgery comprising at least a surgical microscope with at least one digital image sensor, an illumination unit and a control unit.

In the method, a digital image of the observation region is created using the at least one digital image sensor in a digital observation mode of the surgical microscope, said image being observed by way of at least one display. By contrast the observation region is observed through at least one eye piece without digital means being interposed in a non-digital observation mode of the surgical microscope. Moreover, at least two modes of operation are present. In the method according to the invention, the surgical microscope outputs an observation mode signal indicating the observation mode and a mode-of-operation signal indicating the mode of operation. The control unit receives the observation mode signal and the mode-of-operation signal from the surgical microscope and outputs a change signal which prompts the change in the amount of light received by the at least one digital image sensor, the control unit outputting the change signal only if the received observation mode signal and the received mode-of-operation signal indicate a predetermined combination of observation mode and mode of operation.

The claimed method provides the method-type means with which the adjustment options can be improved in the optical system according to the invention. By way of example, the method facilitates a targeted adjustment of the illumination intensity as a result of the illumination intensity being set not only on the basis of the adjusted mode of operation that signals a certain treatment but being set on the basis of one or more defined combinations of mode of operation and observation mode. Moreover, the change signal in this case need not necessarily lead to a change in illumination intensity but may also lead to a change in the exposure duration of the at least one digital image sensor in order to generate a suitable image brightness on the at least one display.

In a special configuration of the method according to the invention, one of the modes of operation is a mode of operation for posterior segment surgery. In this embodiment variant, the change signal causes a reduction in the amount of light received by the at least one digital image sensor, and the control unit outputs the change signal only on the condition that the mode-of-operation signal indicates the mode of operation for posterior segment surgery and the observation mode signal indicates the digital observation mode. Like the optical system according to the invention, the method according to the invention also facilitates an automated reduction in the light intensity received by the digital image sensor in the case of posterior segment surgery in the digital mode of operation. An incorrect setting can be reliably avoided with the aid of the method according to the invention.

The change signal can be output by the control unit to an image sensor controller assigned to the at least one digital image sensor. Upon reception of the change signal, the image sensor controller changes the exposure duration of the at least one image sensor, for example. In the case of the "posterior segment surgery" mode of operation, this change consists of for example a reduction in the exposure duration if the mode-of-operation signal indicates the mode of operation for posterior segment surgery and the observation mode signal indicates the digital observation mode. Since image sensor controllers are present in any case as a rule, this configuration facilitates the software-based update of existing optical systems for eye surgery such that these are able to carry out the method according to the invention.

In an alternative configuration, the change signal is output to an apparatus of the illumination unit for controllably changing the illumination intensity. The apparatus for controllably changing the illumination intensity changes the illumination intensity in the illumination beam path, for example, upon reception of the reduction signal. In relation to the change in the exposure duration of the at least one digital image sensor, this configuration offers the advantage that a change in the form of a reduction in the illumination intensity can not only avoid an excessively bright image on the monitor but can also spare the retina on account of the reduced illumination intensity. The change in the illumination intensity can be implemented with the aid of the attenuator described within the scope of the optical system according to the invention or with the aid of the stop with a controllable aperture described within the scope of the optical system according to the invention.

Within the scope of the method according to the invention, it is advantageous if the change in the illumination intensity is a reduction by a value ranging between 50% and 90%. Since the emission of the illumination light source is not altered within the scope of the present invention, it can still be varied between a minimum value and a maximum value in steps of 5% for example, and so a fine regulation of the brightness displayed on the monitor by way of controlling the emission of the illumination light source still is possible in the case of posterior segment surgery with the aid of at least one digital image sensor, even in the case of a reduction in the illumination intensity by 90%.

Further features, properties and advantages of the invention will become apparent from the following description of exemplary embodiments with reference to the accompanying figures.

Before the invention will be explained in more detail on the basis of FIG. 2, the typical structure of a surgical microscope is described with reference to FIG. 1.

Figure 1:
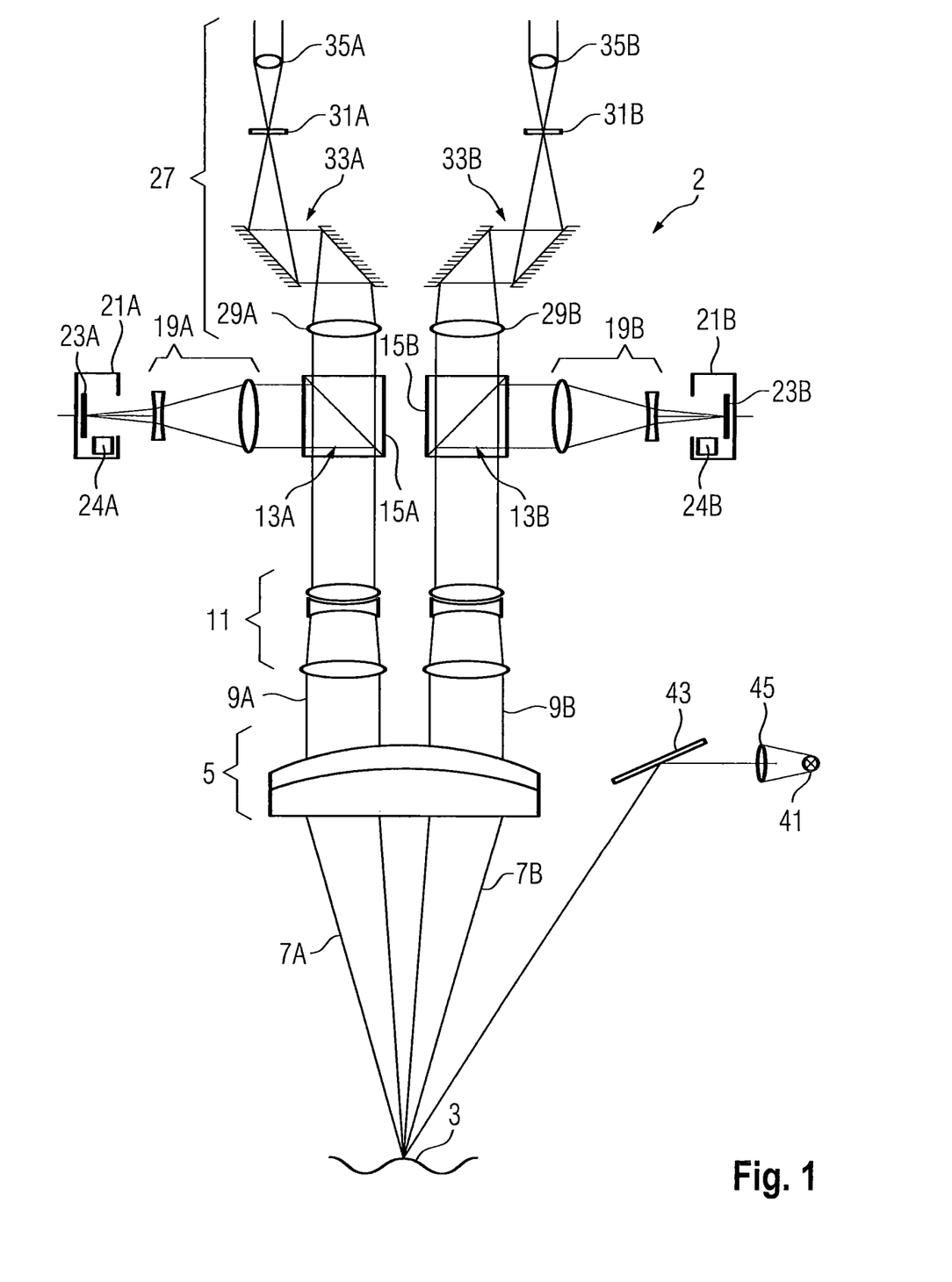
FIG. 1 shows an example of the hardware components of a surgical microscope in a schematic representation.

The surgical microscope 2 shown in FIG. 1 comprises, as essential components, an objective 5 that should face an object field 3, said objective, in particular, being able to be embodied as an achromatic or apochromatic objective. In the present exemplary embodiment, the objective 5 consists of two partial lenses that are cemented to one another and form an achromatic objective. The object field 3 is arranged in the focal plane of the objective 5 such that it is imaged at infinity by the objective 5. Expressed differently, a divergent beam 7 emanating from the object field 3 is converted into a parallel beam 9 during its passage through the objective 5.

A magnification changer 11 is arranged on the observer side of the objective 5, which magnification changer can be embodied either as a zoom system for changing the magnification factor in a continuously variable manner as in the illustrated embodiment, or as what is known as a Galilean changer for changing the magnification factor in a stepwise manner. In a zoom system, constructed by way of example from a lens combination having three lenses, the two object-side lenses can be displaced in order to vary the magnification factor. In actual fact, however, the zoom system also can have more than three lenses, for example four or more lenses, in which case the outer lenses then can also be arranged in a fixed manner. In a Galilean changer, by contrast, there are a plurality of fixed lens combinations which represent different magnification factors and which can be introduced into the beam path alternately. Both a zoom system and a Galilean changer convert an object-side parallel beam into an observer-side parallel beam having a different beam diameter. In the present embodiment, the magnification changer 11 already is part of the binocular beam path of the surgical microscope 1, i.e., it has a dedicated lens combination for each stereoscopic partial beam path 9A, 9B of the surgical microscope 1. In the present embodiment, a magnification factor is adjusted by means of the magnification changer 11 by way of a motor-driven actuator which, together with the magnification changer 11, is part of a magnification changing unit for adjusting the magnification factor.

The magnification changer 11 is adjoined on the observer side by an interface arrangement 13A, 13B, by means of which external appliances can be connected to the surgical microscope 1 and which comprises beam splitter prisms 15A, 15B in the present embodiment. However, in principle, use can also be made of other types of beam splitters, for example partly transmissive mirrors. In the present embodiment, the interfaces 13A, 13B serve to output couple a beam from the beam path of the surgical microscope 2.

In the present embodiment, the beam splitter prisms 15A, 15B serve to each output couple a beam from the partial beam paths 9A, 9B. A camera adapter 19A, 19B with a camera 21A, 21B fastened thereto and equipped with an electronic image sensor 23A, 23B, for example with a CCD sensor or a CMOS sensor, is arranged on each interface 13A, 13B of the interface arrangement. By means of the cameras 21A, 21B, it is possible to record an electronic image and, in particular, a digital image of the tissue region 3. Instead of the camera adapters 19A, 19B and the cameras 21A, 21B fastened thereto, the surgical microscope 2 of the present exemplary embodiment may have fixedly integrated digital image sensors, upstream of each of which there is an optical system for focusing the output coupled beam onto the respective image sensor.

The interface arrangement 13A, 13B is adjoined on the observer side by a binocular tube 27. The latter has two tube objectives 29A, 29B, which focus the respective parallel beam 9A, 9B onto an intermediate image plane 31, i.e., image the observation object 3 onto the respective intermediate image plane 31A, 31B. The intermediate images situated in the intermediate image planes 31A, 31B are finally imaged at infinity in turn by eyepieces 35A, 35B, such that an observer can observe the intermediate image with a relaxed eye. Moreover, an increase in the distance between the two partial beams 9A, 9B is implemented in the binocular tube by means of a mirror system or by means of prisms 33A, 33B in order to adapt said distance to the interocular distance of the observer. In addition, image erection is carried out by the mirror system or the prisms 33A, 33B.

The surgical microscope 2 is additionally equipped with an illumination apparatus, with which the object field 3 can be illuminated with broadband illumination light. To this end, the illumination apparatus in the present embodiment has a white-light source 41, for example a halogen lamp or a gas discharge lamp. The light emanating from the white-light source 41 is directed in the direction of the object field 3 via a deflection mirror 43 or a deflection prism in order to illuminate said field. Furthermore, an illumination optical unit 45 is present in the illumination apparatus, said illumination optical unit ensuring uniform illumination of the entire observed object field 3. However, in the case of posterior segment surgery this illumination apparatus does not serve to illuminate the operating field but—if it is used at all—it serves to illuminate the operating surround.

Reference is made to the fact that the illumination beam path illustrated in FIG. 1 is highly schematic and does not necessarily reproduce the actual course of the illumination beam path. In principle, the illumination beam path can be designed as what is known as oblique illumination, which comes closest to the schematic illustration in FIG. 1. In such oblique illumination, the beam path extends at a relatively large angle (6° or more) with respect to the optical axis of the objective 5 and, as illustrated in FIG. 1, may extend completely outside the objective. Alternatively, however, there is also the possibility of allowing the illumination beam path of the oblique illumination to extend through a marginal region of the objective 5. A further option for the arrangement of the illumination beam path is the so-called 0° illumination, in which the illumination beam path extends through the objective 5 and is input coupled into the objective between the two partial beam paths 9A, 9B, along the optical axis of the objective 5 in the direction of the object field 3. Finally, it is also possible to design the illumination beam path as what is known as coaxial illumination, in which a first illumination partial beam path and a second illumination partial beam path are present. The partial beam paths are coupled into the surgical microscope 2 via one or more beam splitters parallel to the optical axes of the observation partial beam paths 9A, 9B, such that the illumination extends coaxially with respect to the two observation partial beam paths. As a rule, the 0° illumination and the coaxial illumination do not find use in posterior segment surgery.

In the embodiment variant of the surgical microscope 2 shown in FIG. 1, the objective 5 consists only of one achromatic lens. However, use can also be made of an objective lens system composed of a plurality of lenses, in particular what is known as a varioscope objective, by means of which it is possible to vary the working distance of the surgical microscope 2, i.e., the distance between the object-side focal plane and the vertex of the first object-side lens surface of the objective 5, also referred to as front focal distance, by displacing the objective lenses with respect to one another. The object field 3 arranged in the focal plane is imaged at infinity by a varioscope objective, too, and so a parallel beam is present on the observer side.

Figure 2:
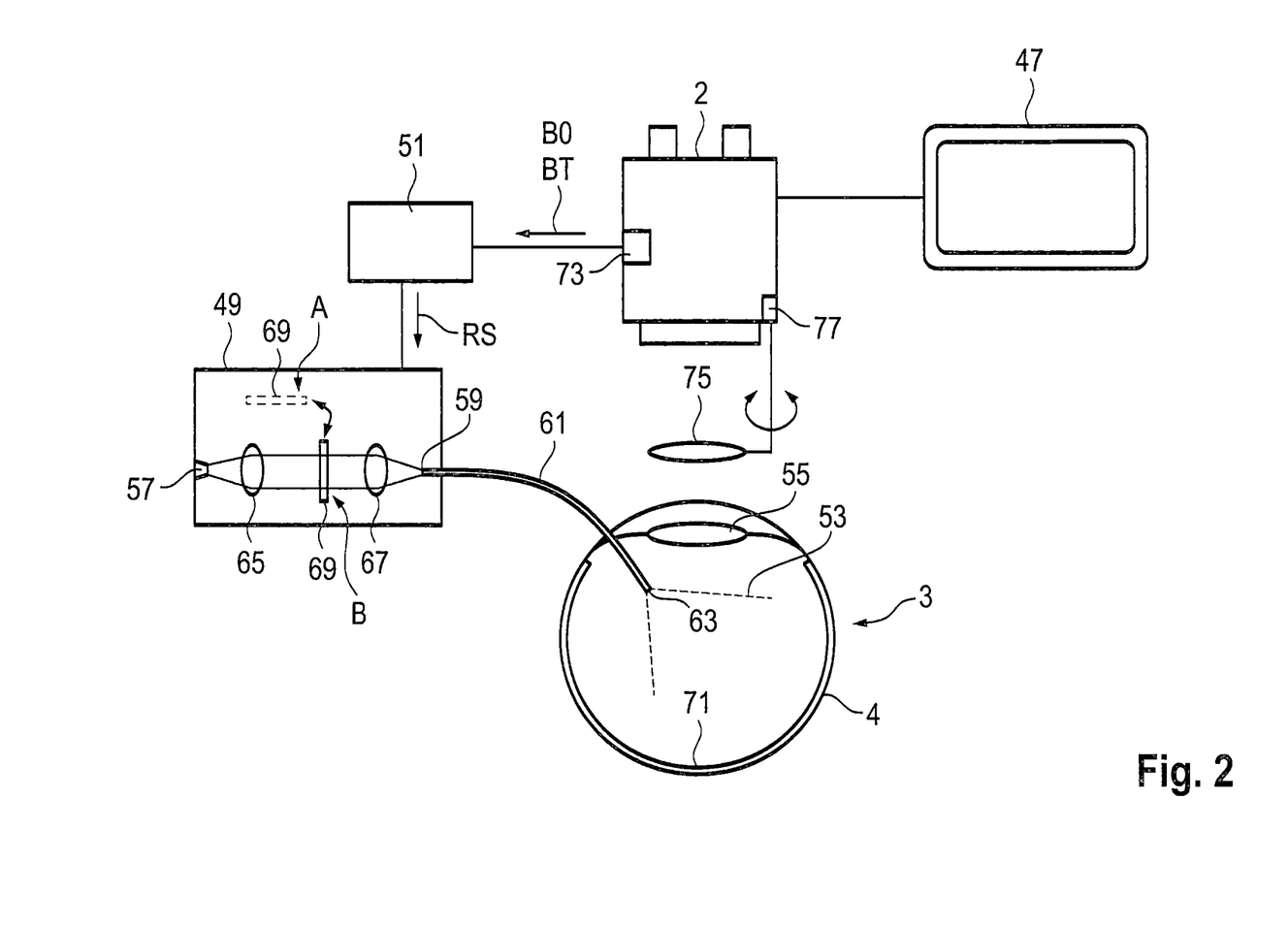
FIG. 2 shows an optical system for eye surgery in a schematic representation.

A surgical microscope as described finds use in the exemplary embodiment of an optical system for eye surgery shown in FIG. 2. In addition to the surgical microscope 2, the optical system of the exemplary embodiment comprises a monitor 47, on which the images recorded by the image sensors 23A, 23B are depicted and are able to be observed in three dimensions by means of 3-D glasses, and a so-called phaco machine which comprises an endoilluminator 49 as an illumination unit, by means of which it is represented in FIG. 2. Moreover, the optical system comprises a control unit 51 which is connected to the surgical microscope 2 and to the phaco machine, to be precise to the endoilluminator 49 of the phaco machine in the present exemplary embodiment. In addition to the endoilluminator 49, the phaco machine also comprises surgical tools (not depicted in FIG. 2) for treatment in the operating field 3, an eye in the exemplary embodiment. In particular, the surgical tools may comprise tools for comminuting the vitreous humor or the lens 55 and for aspirating the vitreous humor fragments or lens fragments. However, it is predominantly the endoilluminator 49 of the phaco machine used to illuminate the eye 3 from the inside during the surgical procedure that is of relevance within the scope of the present invention.

The endoilluminator 49 comprises a light source 57, in the form of an LED in the exemplary embodiment, and optical components 65, 67 with the aid of which the illumination light emanating from the LED 57 is input coupled into the proximal end 59 of an optical fiber 61. Within the scope of posterior segment surgery, the distal end 63 of the optical fiber 61 is introduced into the interior of the eyeball in order to illuminate the posterior segment of the eye from that location. The optical fiber is usually introduced into the interior of the eyeball 4 with the aid of a trocar that is used to puncture the eyeball and that comprises a lumen through which the optical fiber is guided into the interior of the eye. However, the trocar has not been depicted in FIG. 2 for reasons of clarity.

As optical components 65, 67 for input coupling the light emanating from the LED 57 into the proximal end 59 of the optical fiber 61, the endoilluminator 49 comprises a collector 65 which serves to collimate the divergent beam emanating from the LED 57 into a parallel beam and a condenser 67 which focuses the collimated beam onto the distal end 59 of the optical fiber 61. Even though both collector 65 and condenser 67 are represented as single lenses in FIG. 2, the collector 65 and/or the condenser 67 may each consist of a combination of a plurality of lenses.

An attenuator 69 which can be introduced into the collimated beam path and be removed therefrom again is present between the collector 65 and the condenser 67. Should the attenuator 69 be introduced into the illumination beam path it reduces the illumination intensity of the illumination light emanating from the LED 57. In the present exemplary embodiment the attenuator 69 is a neutral density filter which reduces the intensity of the illumination light by a value ranging between 50 percent and 90 percent, typically by a value ranging between 70 and 90 percent and in particular by a value ranging between 80 and 90 percent. As depicted in FIG. 2, the attenuator 69 can be pivoted from a position not within the illumination beam path (position A in FIG. 2) into a position within the collimated beam path (position B). Pivoting the attenuator 69 into position B, that is to say into the collimated beam path of the endoilluminator 49, is necessary, as a rule, if the optical system depicted in FIG. 2 is used in posterior segment surgery and, at the same time, the observation is implemented via the monitor 47 and not via the eyepieces 35A, 35B of the surgical microscope 2. In this case, the intensity of the non-attenuated illumination light would be so high that the image sensors supply an excessively bright image. By pivoting the attenuator 69 into position B there is an attenuation of the illumination light emitted by the endoilluminator 49 into the interior of the eye 3 to a value leading to an appropriate value of the amount of light recorded by the image sensors 23 at their location, and so the exposure duration need not be altered at the image sensors. At the same time, reducing the illumination intensity spares the retina 71 of the treated eye 3.

Even though a neutral density filter as attenuator is pivoted into the collimated beam path in the exemplary embodiment, other attenuators, for example a sieve aperture, may also be pivoted into the collimated beam path instead of the neutral density filter. Moreover, it is not necessary either to design the attenuator to be pivotable. In an alternative embodiment, a stop with a variable aperture, in the case of which the aperture can be altered for the purposes of changing the illumination intensity, can be used as attenuator. By way of example, an iris diaphragm can be used as a stop with a variable aperture.

In the present exemplary embodiment, the surgical microscope 2 has at least two modes of operation, one of which is a mode of operation for posterior segment surgery. Moreover, the surgical microscope 2 has a visual observation mode, in which the treating surgeon observes the eye 3 purely visually through the eyepieces 35A, 35B and the optical system of the surgical microscope 2, and a digital observation mode, in which the treating surgeon observes the eye 3 on the monitor 47. Electronic components 73, 77 of the surgical microscope 2 register the observation mode set on the surgical microscope 2 and the mode of operation of the surgical microscope 2. The observation mode can be registered on the basis of the settings undertaken on the operating console of the surgical microscope 2. In the present exemplary embodiment, the mode of operation is registered on the basis of an ophthalmic loupe 75 which is capable of being pivoted into the observation beam path and can be pivoted into the observation beam path between the objective of the surgical microscope 2 and the eye 3. A sensor 77 recognizes the pivot position in which the ophthalmic loupe 75 is pivoted into the observation beam path and hence recognizes the "posterior segment surgery" mode of operation. In other pivot positions, a "no posterior segment surgery" mode of operation is registered in the present exemplary embodiment. Naturally, the mode-of-operation signal can also be registered on the basis of other processes instead of the detection of the pivot position of the ophthalmic loupe 75; by way of example, should the operating console of the surgical microscope allow a "posterior segment surgery" mode of operation to be set, the mode of operation can be registered on the basis of the setting undertaken on the operating console.

The registered observation mode and the registered mode of operation are output in the form of an observation mode signal BO and a mode-of-operation signal BT to the controller 51 and the controller 51 generates a change signal if the mode-of-operation signal indicates the mode of operation for posterior segment surgery and the observation mode signal indicates the digital observation mode. In the present exemplary embodiment, the change signal is a reduction signal RS which prompts a reduction in the illumination intensity by pivoting the attenuator 69 into the illumination beam path. The controller 51 then outputs this reduction signal RS to the endoilluminator 49 which, upon reception of the reduction signal RS, pivots the attenuator 69 from position A to position B such that said attenuator is situated in the illumination beam path of the endoilluminator 49. In an alternative embodiment, the reduction signal may lead to a reduction in the size of the aperture of a stop with a variable aperture instead of to the pivoting of an attenuator 69 into the illumination beam path. However, the reception of the reduction signal in both cases has as a consequence that the illumination intensity is reduced, leading to a reduction in the amount of light received by the digital image sensors 23A, 23B and to the retina 71 being spared.

The described reduction in the illumination intensity assumes that the controller 51 receives both an observation mode signal BO indicating the digital observation mode and a mode-of-operation signal BT indicating the "posterior segment surgery" mode of operation. Should on the other hand the observation mode signal indicate the visual observation mode, the controller 51 does not output a reduction signal RS to the endoilluminator 49 of the phaco machine, independently of whether the mode-of-operation signal BT indicates the "posterior segment surgery" mode of operation or the "no posterior segment surgery" mode of operation. Likewise, the controller 51 outputs no reduction signal RS to the endoilluminator 49 of the phaco machine if the mode-of-operation signal indicates "no posterior segment surgery", independently of whether the observation mode signal BO indicates the digital observation mode or the visual observation mode.

In the exemplary embodiment illustrated in FIG. 2, the amount of light received by the digital image sensors 23A, 23B is reduced by way of a reduction of the illumination light emitted by the endoilluminator 49 of the phaco machine. In an alternative embodiment, the reduction in the amount of light received by the digital image sensors 23A, 23B is implemented by reducing the exposure duration of the digital image sensors 23A, 23B. In this case, the control unit 51 does not output the reduction signal RS to the endoilluminator 49 of the phaco machine 49 but to the cameras 21A, 21B or the image sensor controllers 24A, 24B thereof, by means of which the image sensors 23A, 23B are controlled. In this case, too, the reduction signal RS is output only if the observation mode signal BO indicates the digital observation mode and the mode-of-operation signal BT indicates the "posterior segment surgery" mode of operation. The reduction signal RS is not output in other signal combinations.

The present invention has been described in detail on the basis of an exemplary embodiment for explanatory purposes. However, a person skilled in the art recognizes that there can be deviations from the embodiment within the scope of the invention. For example, the control unit 51 is depicted as an independent unit in FIG. 2. However, it may also be integrated in the phaco machine or, particularly if the reduction in the amount of light received by the digital image sensors should be attained by reduction in the exposure duration, in the surgical microscope. However, even if the reduction in the amount of light received by the image sensors is caused by a reduction in the illumination intensity the control unit may be integrated in the surgical microscope. Moreover, a person skilled in the art recognizes that it is possible to deviate from the variant of the surgical microscope depicted in FIG. 1 provided said surgical microscope permits both a visual observation mode and a digital observation mode. Therefore, the present invention is not intended to be limited by the exemplary embodiment but rather only by the appended claims.

The invention claimed is:

1. An optical system for eye surgery, comprising at least a surgical microscope, an illumination unit for emitting illumination light, and a control unit,
the surgical microscope comprising:
at least one digital image sensor,
at least one eye piece,
a digital observation mode in which a digital image of the observation region is created using the at least one digital image sensor, said image being observed by way of at least one display,
a non-digital observation mode in which the observation region is observed through the at least one eye piece without digital means being interposed, and
at least two modes of operation,
and with
the surgical microscope being configured to output an observation mode signal indicating the employed observation mode and a mode-of-operation signal indicating the employed mode of operation,
the control unit being configured to receive the observation mode signal and the mode-of-operation signal from the surgical microscope and to output a change signal which prompts a change in the amount of light received by the at least one digital image sensor, the control unit being configured to output the change signal when the received observation mode signal and the received mode-of-operation signal indicate a predetermined combination of observation mode and mode of operation.

2. The optical system as claimed in claim 1, wherein one of the modes of operation is a mode of operation for posterior segment surgery, the change signal is suitable for prompting a reduction in the amount of light received by the at least one digital image sensor and the output of the change signal requires that the mode-of-operation signal indicates the mode of operation for posterior segment surgery and the observation mode signal indicates the digital observation mode.

3. The optical system as claimed in claim 2, wherein the surgical microscope is configured to recognize whether an ophthalmic loupe has been pivoted into the observation beam path and to output the mode-of-operation signal indicating the mode of operation for posterior segment surgery upon recognition of an ophthalmic loupe pivoted into the observation beam path.

4. The optical system as claimed in claim 2, wherein the illumination unit is an endoilluminator with a light guide that is insertable into the eye for the purposes of illuminating the posterior segment of the eye.

5. The optical system as claimed in claim 1, wherein an image sensor controller is assigned to the at least one digital image sensor and is connected to the control unit for outputting the change signal, and the image sensor controller is configured to change the exposure duration of the at least one digital image sensor upon reception of the change signal.

6. The optical system as claimed in claim 1, wherein
the illumination unit comprises an apparatus for controllably changing the illumination intensity,
the control unit is configured to output the change signal to the apparatus for controllably changing the illumination intensity, and
the apparatus for controllably changing the illumination intensity is configured to change the illumination intensity upon reception of the change signal.

7. The optical system as claimed in claim 6, wherein the apparatus for controllably changing the illumination intensity comprises at least one attenuator which is able to controllably be introduced into the illumination beam path of the illumination unit or controllably be removed therefrom, the apparatus being configured to introduce the attenuator into the illumination beam path or remove it therefrom upon reception of the change signal.

8. The optical system as claimed in claim 6, wherein the apparatus for controllably changing the illumination intensity comprises a stop with a controllably variable aperture arranged in the illumination beam path of the illumination unit, said stop being configured to alter the aperture upon reception of the change signal.

9. The optical system as claimed in claim 6, wherein the apparatus for controllably changing the illumination intensity facilitates a reduction in the illumination intensity by a value ranging between 50% and 90%.

10. A method for changing the amount of light received by a digital image sensor in an optical system for eye surgery comprising at least a surgical microscope with at least one digital image sensor, an illumination unit and a control unit, wherein
a digital image of the observation region is created using the at least one digital image sensor in a digital observation mode of the surgical microscope, said image being observed by way of at least one display,
the observation region is observed through at least one eye piece without digital means being interposed in a non-digital observation mode of the surgical microscope, at least two modes of operation are present,
with
    the surgical microscope outputting an observation mode signal indicating the observation mode and a mode-of-operation signal indicating the mode of operation,
    the control unit receiving the observation mode signal and the mode-of-operation signal from the surgical microscope and outputting a change signal which prompts the change in the amount of light received by the at least one digital image sensor,
    the control unit outputting the change signal when the received observation mode signal and the received mode-of-operation signal indicate a predetermined combination of observation mode and mode of operation.

11. The method as claimed in claim 10, wherein one of the modes of operation is a mode of operation for posterior segment surgery, the change signal prompts a reduction in the amount of light received by the at least one digital image sensor and the control unit outputs the change signal only on the condition that the mode-of-operation signal indicates the mode of operation for posterior segment surgery and the observation mode signal indicates the digital observation mode.

12. The method as claimed in claim 10, wherein the indication of the mode of operation for posterior segment surgery is triggered by the mode-of-operation signal by pivoting an ophthalmic loupe into the observation beam path.

13. The method as claimed in claim 10, wherein the change signal is output to an image sensor controller assigned to the at least one digital image sensor, said image sensor controller changing the exposure duration of the at least one image sensor upon reception of the change signal.

14. The method as claimed in claim 10, wherein the change signal is output to an apparatus of the illumination unit for controllably changing the illumination intensity, which changes the illumination intensity upon reception of the change signal.

15. The method as claimed in claim 14, wherein the change in the illumination intensity is a reduction by a value ranging between 50% and 90%.

* * * * *